United States Patent
Sekimoto

(10) Patent No.: US 6,814,958 B1
(45) Date of Patent: Nov. 9, 2004

(54) FOOD COMPOSITIONS, COMPOSITIONS FOR ORAL CAVITY AND MEDICINAL COMPOSITIONS FOR PREVENTING OR TREATING PERIODONTOSIS AND METHOD FOR PREVENTING OR TREATING PERIODONTOSIS

(75) Inventor: Yukiyo Sekimoto, Osaka (JP)

(73) Assignee: Sunstar Inc., Osaka (JP)

( * ) Notice: Subject to any disclaimer, the term of this patent is extended or adjusted under 35 U.S.C. 154(b) by 0 days.

(21) Appl. No.: 09/694,334

(22) PCT Filed: Apr. 23, 1999

(86) PCT No.: PCT/JP99/02179

§ 371 (c)(1),
(2), (4) Date: Apr. 24, 1998

(87) PCT Pub. No.: WO99/55298

PCT Pub. Date: Nov. 4, 1999

(30) Foreign Application Priority Data

Apr. 24, 1998 (JP) .......................... 10-115201

(51) Int. Cl.⁷ ............................ A61K 7/26; A61K 35/78
(52) U.S. Cl. .......................... 424/58; 424/49; 424/729; 424/732; 424/766
(58) Field of Search .............. 424/58, 52, 49, 424/729, 732, 766; 132/323

(56) References Cited

U.S. PATENT DOCUMENTS 5,032,384 A * 7/1991 Yeh et al. ............. 424/49
5,683,678 A * 11/1997 Heckert et al. ............. 424/52
5,875,799 A * 3/1999 Petrus et al. ............. 132/323

FOREIGN PATENT DOCUMENTS

| JP | 57-32219 A | | 2/1982 |
|---|---|---|---|
| JP | 57139013 | * | 8/1982 |
| JP | 62-273910 A | | 11/1987 |
| JP | 63-141921 A | | 6/1988 |
| JP | 2-270815 A | | 11/1990 |
| JP | 4-77424 A | | 3/1992 |
| JP | 404273814 | * | 9/1992 |
| JP | 4-290819 A | | 10/1992 |
| JP | 040473844 | * | 10/1993 |
| JP | 06179609 | * | 6/1994 |
| JP | 8-81380 A | | 3/1996 |
| JP | 08081380 | * | 3/1996 |
| JP | 8-104628 A | | 4/1996 |
| JP | 9-107917 A | | 4/1997 |
| JP | 10330282 | * | 12/1998 |

* cited by examiner

Primary Examiner—Christopher R. Tate
Assistant Examiner—Randall Winston
(74) Attorney, Agent, or Firm—Sughrue Mion, PLLC

(57) ABSTRACT

Food compositions, oral compositions and pharmaceutical compositions for preventing or treating periodontosis, the compositions comprising (A) one or more extracts containing natural polyphenol; and (B) one or more members selected from the group consisting of vitamin C, vitamin E, vitamin A and beta-carotene; and methods for preventing or treating periodontosis using the above compositions.

12 Claims, No Drawings

FOOD COMPOSITIONS, COMPOSITIONS FOR ORAL CAVITY AND MEDICINAL COMPOSITIONS FOR PREVENTING OR TREATING PERIODONTOSIS AND METHOD FOR PREVENTING OR TREATING PERIODONTOSIS

TECHNICAL FIELD

The present invention relates to food compositions, oral compositions and pharmaceutical compositions for preventing or treating periodontosis and methods for preventing or treating periodontosis by using these compositions.

BACKGROUND ART

Matrix metalloprotease (hereinafter referred to as "MMPs") is a generic name of extracellular matrix protease which are characterized by having zinc (II) ion at their active sites. The metabolism of this extracellular matrix is adjusted mainly by the balance between the MMPs and metalloprotease inhibitors (TIMP) which is specific for MMPs and is derived from organizations. It is known that periodontosis such as the periodontitis is associated with the structural anomaly of the extracellular matrix components and the loss of metabolism balance such as synthesis and degradation of the extracellular matrix component resulting from the abnormal expression of MMPs.

More than 10 enzyme molecules are know as MMPs, including collagenase (MMP-1 and 8), stromelysin (MMP-3), gelatinase (MMP-2 and 9) and the like (Yoshihara, Niina: Inflammation and Immunity, 2, 177–185, 1994). These are produced by various kinds of cells.

In periodontosis such as gingivitis and periodontitis, MMPs seems to be deeply concerned in development and progress of periodontosis. It is suggested that MMPs concerning the organization destruction of gingivitis, periodontitis and like periodontosis are collagenase and gelatinase mainly produced by human gingival epithelium cells, gingiva fibroblasts and periodontal membrane cells. More specifically, it is thought as follows: periodontosises such as gingivitis and periodontitis are caused by the infection of periodontium with specific periodontosis original fungus (*P. gingivalis*). MMPs are produced by epithelial cells, gingiva fibroblasts and periodontal membrane cells in the periodontium which have received external stimulation by the pathogenic fungi. As the result, a periodontal membrane structure which connects teeth and periodontium is destroyed in cell-derived MMPs. Mainly by this destruction, the periodontosis occurs and develops (M. Kylmaniemi et al: J. Dent Res., 75:919–926, 1996). It is also suggested that the activity of the MMPs derived from periodontium is easily increased by one's smoking habit, development of diabetes and other factors which change the immune responsiveness of organisms, leading to the increased rate of the development and progress of gingivitis, periodontitis and like periodontosis.

Therefore, it is considered that the inhibitor of MMPs is effective for treatment and prevention of periodontosis such as periodontitis and gingivitis and the like. For example, there is a report on the use of tetracycline and its modification, which reportedly inhibit the MMPs derived from gingiva fibroblasts and epithelial cells, in the treatment of periodontitis (L. H. Nip et al: J. Periodont Res., 28: 379–385, 1993).

However, tetracycline-based antibiotics, which are synthetic substances, have particular side effects and risks of resistant microbe appearance in the human body. Considering this fact, it is not desirable that these antibiotics are taken in the long term for treating or preventing periodontosis such as periodontitis. Therefore, the desired MMPs inhibitor is of natural origin and has few side effect by taking the inhibitor, and has inhibitory effects on the MMPs derived from periodontium. Moreover, sufficient inhibitory effects on MMPs must be demonstrated at a normal and appropriate dose.

As the MMPs inhibitors of natural origin, for example, flavones or anthocyanidins of natural origin reportedly has the MMPs inhibitory effects (Japanese Unexamined Patent Publication No. 1996-104628). Reported inhibitors of natural origin on one kind of the MMPs, collagenase, include schizonepeta herb extract, mint extract (Japanese Unexamined Patent Publication No. 1994-183990), nordihydroguaiaretic acid (Japanese Unexamined Patent Publication No. 1992-217626) and polyporenic acid C (Japanese Unexamined Patent Publication No. 1997-40552). In addition, tetracyclic triterpene 20-carboxy-16-hydroxy-21-nor-5 $\alpha$-7,9 (11)-lanostadien-3,24-dione which is extracted from *Daedalea dickiusi* and refined is also reported to have an inhibitory effect on collagenase (No. 1997-235293).

M. Makimura et al reported in J. Periodontol., 64(7): 630–636, 1993 that catechins contained in tea showed the inhibitory effects on collagenase derived from prokaryotic and eukaryotic cells and on collagenase derived from gingival crevicular effusion of periodontosis patients.

Furthermore, Japanese Examined Patent Publication No. 1992-27204 reported the preventive effects of polyphenol extracted from green tea on dental caries and periodontosis.

A supplementary food product (trade name: Body Language, Oxyfresh Co., U.S.A.) appealing its anti-inflammatory effect on the gingiva is commercially available in the U.S.A. This supplementary food contains a grape seed extract which reportedly exhibits the inhibitory effect on some of the collagenase derived from fungus (L. Robert et al: Path. Biol, 38:608,1990) and coenzymes Q10.

Meanwhile, focusing on antioxidant effects, Japanese Unexamined Patent Publication No. 1995-196534 reports the synergistic antioxidant effect of the activity of the combination of hydrophilic polyphenol having the structure similar to that of catechin or flavonolignan (e.g., proanthocyanidin) and lipophilic carotenoid or lipophilic procarotenoid (e.g., vitamin E).

DISCLOSURE OF INVENTION

An object of the present invention is to provide a composition effective in preventing or treating periodontosis, particularly effective in preventing and treating periodontosis aggravated by smoking, particularly a food composition, oral composition and pharmaceutical composition.

The inventors of the present invention conducted extensive research and found the following: the MMPs inhibitory effect is increased by using an extract containing natural polyphenol in combination with at least one of vitamin C (and its salts), vitamin E, vitamin A and beta-carotene. They also found that excellent periodontosis preventive or therapeutic effect can be achieved by the composition containing these extract and vitamins. The present invention was accomplished based on these findings.

Additionally, it was found that the addition of a plant extract having an antibacterial activity to the above composition which comprises the extract containing the natural polyphenol and vitamins can remove the stimulation for the periodontium of the periodontosis original fungus, whereby the preventive effect or therapeutic effect can be increased.

Moreover, the inventors of the present invention found that the combined use of the extract containing the natural polyphenol and the above vitamins in the presence of nicotine can further improve the inhibitory effect on the increase in MMPs concentration. Nicotine is a main stimulant found in cigarette smoke. The results of in vitro test reveal that the stimulation of nicotine produces adverse effects such as inhibition of periodontium cell proliferation, increased production of collagenase and the like. Accordingly, smokers tend to contract periodontosis and suffer fast progress of the same induced by smoking. Even a passive smoker, that is, a person who is under the environment where nicotine exists, such as the spouse of a smoker, tends to contract periodontosis and suffer fast progress of the same as well as the smokers. Based on the above, the inventors of the present invention found that the increase in the MMPs concentration in the oral cavity induced by smoking can be effectively inhibited by the composition which comprises the extract containing the natural polyphenol and the above vitamins.

The present invention provides the inventions listed below:

Item 1. A composition for preventing or treating periodontosis comprising (A) at least one member selected from extracts containing natural polyphenol and (B) at least one member selected from the group consisting of vitamin C or its salts, vitamin E, vitamin A and beta-carotene.

Item 2. The composition according to item 1 which is a food composition.

Item 3. The composition according to item 1 which is an oral composition.

Item 4. The composition according to item 1 which is a pharmaceutical composition.

Item 5. The composition according to item 1, (A) the extracts containing the natural polyphenol being at least one member selected from the group consisting of a grape seed extract, a tea extract, a blueberry extract and a silymarin extract.

Item 6. The composition according to item 1 which further comprises (C) an antibacterial plant extract.

Item 7. The composition according to item 6, (C) the antibacterial plant extract being at least one member selected from the group consisting of an oil-soluble glycyrrhiza extract and a mulberry bark extract.

Item 8. The composition according to item 1 which has an inhibitory activity on Matrix metalloprotease production by periodontium cells which are stimulated by nicotine, and is particularly effective for smokers.

Item 9. A method for preventing or treating periodontosis by ingesting or administering an effective amount of a composition comprising (A) at least one member selected from extracts containing natural polyphenol; and (B) at least one member selected from a group consisting of vitamin C and its salts, vitamin E, vitamin A and beta-carotene.

Item 10. The method according to item 9, (A) the extract containing the natural polyphenol being at least one member selected from the group consisting of a grape seed extract, a tea extract, a blueberry extract and a silymarin extract.

Item 11. The method according to item 9 which further contains (C) an antibacterial plant extract.

Item 12. The method according to item 11, wherein (C) the antibacterial plant extract is at least one member selected from the group consisting of an oil-soluble glycyrrhiza extract and a mulberry bark extract.

Item 13. The method according to item 9 which comprises ingestion or administration to smokers.

Item 14. A method for preventing or treating periodontosis which comprises application to oral cavity an effective amount of (A) at least one member selected form extracts containing natural polyphenol; and (B) at least one member selected from the group consisting of vitamin C and its salts, vitamin E, vitamin A and beta-carotene.

Item 15. The method according to item 14, wherein (A) the extracts containing the natural polyphenol is at least one member selected from a group consisting of a grape seed extract, a tea extract, a blueberry extract and a silymarin extract.

Item 16. The method according to item 14 which further comprises (C) an antibacterial plant extract.

Item 17. The method according to item 16, wherein (C) the antibacterial plant extract is at least one member selected from the group consisting of an oil-soluble glycyrrhiza extract and a mulberry bark extract.

Item 18. The method according to item 14 which is applied to oral cabity of smoker.

The present invention is described in details in the following.

In the present invention, by the term "natural polyphenol" is meant polyphenol contained in an extract derived from animals and plants found in nature, in other words, polyphenol of natural origin.

The extract containing the natural polyphenol for use in the present invention is not particularly limited insofar as it exhibits a desired effect when used in combination with vitamins for use in the present invention. Examples of the extracts include those containing natural polyphenol having a flavonoid structure, catechol, phloroglucin and the like. Particularly preferable is the extract which contains the natural polyphenol having an MMPs inhibitory activity as natural polyphenol.

Examples of the natural polyphenol having the MMPs inhibitory activity include those having the inhibitory activity on the MMPs derived from cells such as periosteum and articular cartilaginous tissues in chronic rheumatism and osteoarthritis; cornea tissues; periodontium; cancer tissues and the like. Among these, particularly preferable is the natural polyphenol having the inhibitory activity on the MMPs derived from periodontium cells.

Examples of the natural polyphenol having the inhibitory activity on the MMPs derived from periodontium cells include a natural polyphenol having a flavonoid structure.

Examples of the natural polyphenol having the flavonoid structure include proanthocyanidin; epigallocatechin, epicatechin, gallocatechin and like catechins; anthocyanidins, anthocyanins and the like.

Examples of the extract containing the natural polyphenol for use in the composition of the present invention include those containing the natural polyphenol such as a grape seed extract obtained from grape seeds, a tea extract obtained from tea, a blueberry extract obtained from blueberries, a silymarin extract obtained from thistle, and the like. Among these, the grape seed extract is preferably used.

In the present invention, the extract containing the natural polyphenol may be used singly or in combination of two or more kinds. When using two or more extracts in combination, it is preferable to use the grape seed extract with other extracts containing the natural polyphenol. Particularly preferable are the combinations of the grape seed extract and the tea extract; the grape seed extract and the blueberry extract; and the grape seed extract and the silymarin extract. Among them, the combination of the grape seed extract and the tea extract is more favorable.

The amount of the extract containing the natural polyphenol in the composition of the present invention is not limited insofar as it is effective in preventing or treating periodontosis. For example, on a dry weight basis of the extract, the proportion of the extract is preferably about 0.0005–75% by weight, more preferably about 0.001–40% by weight, based on the total weight of the composition. The proportion is preferably about 0.01–20% by weight when the composition of the present invention is used as a food composition, whereas the proportion is preferably about 0.01–1% by weight when the composition is used as an oral composition.

As the extract containing the natural polyphenol for use in the present invention, the extract prepared by conventional methods can be used without limitation insofar as it can produce the desired effects of the present invention.

Examples of solvents for extracting the extract containing the natural polyphenol include water; methanol, ethanol, propanol, butanol and like alcohols; ethyl acetate and like lower alkyl esters; benzene, hexane and like hydrocarbons; ethyl ether, acetone, acetic acid and like conventionally known solvents. These solvents may be used singly or in combination of two or more kinds.

Extracting operation may be carried out by conventional methods which are usually employed.

In the present invention, the extract liquid obtained by the above-mentioned conventional methods may be used as it is, or may be further concentrated, if necessary. The extract liquid may also be refined before use by conventional methods such as countercurrent distribution method, liquid chromatography and the like.

In the present invention, the extract containing the natural polyphenol can be prepared as s dry product. The method for producing the dry product containing the natural polyphenol is not limited. For example, the plant extract liquid obtained by the above method can be processed into a dry plant extract by common methods such as vacuum drying, freeze drying and the like.

The grape seed extract which is useful as the extract containing the natural polyphenol in the present invention is that obtained from the seeds of European grape (*Vitis vinifera*) and that containing, as polyphenols, proanthocyanidin and anthocyanins, i.e., the polyphenols having MMPs inhibitory activities.

The grape seed extract for use in the present invention may be obtained, for example, by the above conventional methods, or by the methods disclosed in Japanese Examined Patent Publication No. 1994-31208, Japanese Unexamined Patent Publication Nos. 1988-162685, 1991-200781, 1990-48593 and 1991-99090, among others.

The grape seed extracts as mentioned in these publications are commercially available as foodstuffs from KIKKO-MAN CORPORATION (trade name: KPA, Gravinol) and Indina Corporation (trade name: Loycoselect).

When the composition of the invention contains the grape seed extract, the amount of the grape seed extract is not limited insofar as the desired effect can be achieved. On a dry weight basis of the extract, the amount of the grape seed extract is preferably about 0.005–75% by weight, more preferably about 10–50% by weight, based on the total amount of the composition of the invention. When the grape seed extract is used in combination with other extracts containing the natural polyphenol, the amount of the extracts are not particularly limited. Preferably, the grape seed extract is used in the above-specified amount, while other extracts containing the natural polyphenol are used in an amount of about 0.005–75% by weight, preferably about 10–50% by weight on a dry weight basis of the extract, based on the total amount of the composition of the invention. When the grape seed extract is used in combination with other extracts containing the natural polyphenol, the preferable amount of other extracts containing the natural polyphenol to be used is as follows: about 0.01–40% by weight in case the composition of the invention is used as a food composition; or about 0.01–5% by weight in case the composition of the invention is used as an oral composition.

When the composition of the invention containing the grape seed extract are prepared as solid forms or solids formulations such as troches, tablets, capsules, candies, chewing gum and the like, it is preferable to use the grape seed extract in an amount of about 0.5–20% by weight, particularly about 1–10% by weight, on a dry weight basis of the extract. When the composition of the invention containing the grape seed extract is prepared as a liquid form or liquid formulation such as juices, the grape seed extract is preferably used in an amount of about 0.005–0.5% by weight on a dry weight basis of the extract.

In the present invention, the raw material of the tea extract can be selected from common tea for beverage use (*Camellia sinensis*) including green tea, oolong tea, black tea, pu-erh tea and the like. The tea extract contains, as the natural polyphenol, epigallocatechins, epicatechins, gallocatechins and like catechins having MMPs inhibitory activities. In the present invention, preferably used is the tea extract containing these polyphenols in the concentration of 30% by weight or higher, particularly 65% by weight or higher. The tea extract, when used in the present invention, may be obtained, for example, by the aforementioned conventional methods or by the methods as disclosed in Japanese Unexamined Patent Publications Nos. 1989-90124 and 1989-265023.

The tea extract is commercially available from MITSUI NORIN CO., LTD. (trade name: Polyphenon) and TAIYO KAGAKU CO., LTD. (trade name: Sunphenon).

The amount of the tea extract, when used in the composition of the invention, is not limited insofar as the desired effect can be achieved. For example, the preferable amount is, on a dry weight basis of the extract, about 0.005–75% by weight, particularly about 10–50% by weight, based on the total amount of the composition of the invention. When the composition of the invention is prepared as solids or solid formations such as troches, tablets, capsules, candies, chewing gum and the like, the proportion of the extract is preferably about 0.5–20% by weight, particularly about 1–10% by weight.

The blueberry extract can be obtained from various kinds of blueberries as raw materials such as *Vaccinium myrtillus, Vaccinium angustifolium, Vaccinium australe, Vaccinium corymbosum, Vaccinium ashei* and the like, and contains, as polyphenol, anthocyanidins, i.e., the polyphenols having MMPs inhibitory activities. When using the blueberry extract in the present invention, usable are, for example, those extracted by the conventional methods as mentioned in the above. For instance, a dry product of the blueberry extract extracted by alcohol-water solvent is commercially available from Indina Corporation. This dry product can also used in the present invention.

When the silymarin extract is used in the present invention, usable are those which are extracted from the raw materials such as *Silybum marianum* Gaertn, *Carduus mari-*

*anum* L. and like thistles by the conventional methods as mentioned in the above. Further, the silymarin extract which is commercially available form Api Co., Ltd. and Indina Corporation can be used in the present invention.

The composition of the invention can also contain, in addition to the extract containing the natural polyphenol, the natural polyphenol having MMPs inhibitory activities contained in the foregoing extracts, together with at least one member selected from the group consisting of vitamin C, vitamin E, vitamin A, beta-carotene and their salts and derivatives, which are listed below.

Examples of the active ingredient, i.e., the natural polyphenol having MMPs inhibitory activities contained in the extract include proanthocyanidin; epigallocatechin, epicatechin, gallocatechin and like catechins; anthocyanidins, anthocyanins and the like. These ingredients can be used singly or in combination of two or more kinds.

Furthermore, it is possible to substitute the extract containing the natural polyphenol by at least one the natural polyphenol having the MMPs inhibitory activities contained in the above-mentioned extracts, together with one or more members selected from the group consisting of vitamin C, vitamin E, vitamin A and beta-carotene, and use the resulting composition as a food composition, an oral composition or a pharmaceutical composition for treating or preventing periodontosis.

In the composition containing the natural polyphenol having MMPs inhibitory activities in place of the extract containing the natural polyphenol, the conditions as listed below are the same as those of the compositions, which uses the extract containing the natural polyphenol in combination with vitamins for use in the present invention: the conditions are kinds and amounts of vitamin C and like vitamins, kinds and amounts of other ingredients; the form or formation of the composition; and the preparation method of the composition, among other conditions. The amount of the natural polyphenol to be added to the above composition is not particularly limited and can be suitably selected as far as the desired effect of the present invention can be achieved. However, it is preferable that the amount is similar to that of the natural polyphenol contained in the composition having the above-specified amount of the extract containing the natural polyphenol.

In the composition of the present invention, used in combination with the extract containing the natural polyphenol is at least one member selected from the group consisting of vitamin C (VC: L-ascorbic acid) and its salts, vitamin E (VE: tocopherol and its derivatives), vitamin A and beta-carotene (hereinafter referred to as "vitamins for use in the present invention"). Examples of the salts of the vitamin C (L-ascorbic acid) include sodium salt, calcium salt, ferrous salt, stearate, palmitate and like derivatives. The derivatives of the vitamin E include $\alpha$-, $\beta$-, $\gamma$- and $\delta$-tocotrienol.

In the composition of the present invention, the salts or derivatives of vitamin A and vitamin E may be used as the vitamins for use in the present invention insofar as it produces the desired effects. Examples of the vitamin A derivatives include $C_{2-20}$ fatty acid esters of vitamin A and the like.

These vitamins for use in the present invention can be used singly or in combination of two or more kinds.

When two or more vitamins for use in the present invention are selected, examples of the combinations of the vitamins include vitamin C (or its salts) and vitamin E; vitamin C (or its salts) and vitamin A; vitamin C (or its salts) and beta-carotene; vitamin E and vitamin A; vitamin E and beta-carotene; vitamin A and beta-carotene; vitamin C (or its salts), vitamin E and vitamin A; vitamin C (or its salts), vitamin E and beta-carotene; vitamin C (or its salts), vitamin A and beta-carotene; vitamin E, vitamin A and beta-carotene; and vitamin C (or its salts), vitamin E, vitamin A and beta-carotene. In these combinations, vitamin A and vitamin E may be replaced with their derivatives or salts.

In the composition of the present invention, the amount of vitamin C and its salts, vitamin E, vitamin A and beta-carotene is not limited insofar as the effect of the present invention can be achieved, and is preferably about 0.0005–50% by weight as the total amount of the vitamins for use in the present invention, based on the total amount of the composition of the present invention.

The amount of the vitamins, as single vitamin or the combination of two or more vitamins, is preferably about 0.005–50% by weight, more preferably about 5–15% by weight in case of vitamin C and its salts; preferably about 0.0005–10% by weight, more preferably about 0.05–5% by weight in case of vitamin E; preferably about 0.05–20% by weight, more preferably about 0.5–5% by weight in case of vitamin A and beta-carotene.

In the composition of the present invention, the ratio of the extract containing the natural polyphenol to the vitamins for use in the present invention is not limited insofar as an object of the present invention can be achieved. Preferably, the weight ratio of the extract and vitamins are about 200:1–1:100, particularly about 10:1–1:10, more particularly about 3:1–1:4. In particular, when vitamin C only is combined with the extract containing the natural polyphenol, the weight ratio of the extract containing the natural polyphenol to the vitamin C is about 100:1–1:100, particularly about 10:1–1:4, more particularly about 5:1–1:3 so that the extract containing the natural polyphenol can exert its highest effectiveness. Therefore, the highest preventive or therapeutic effects on periodontosis can be achieved in the above ranges of the weight ratio of the extract and the vitamin C.

The composition of the present invention may further contain an antibacterial plant extract, in addition to the extract containing the natural polyphenol and the vitamins for use in the present invention. Adding the antibacterial plant extract to the composition allows the composition to remove the stimulating activity on periodontium by the periodontosis pathogenic fungi. Therefore, it is preferable to add the antibacterial plant extract to the composition of the invention because the preventive or therapeutic effects on periodontosis of the composition are increased.

Examples of the antibacterial plant extract for use in the present invention include oil soluble glycyrrhiza extract, mulberry bark extract and the like. The oil soluble glycyrrhiza extract is extracted from glycyrrhiza as a raw material by a conventional manner using ethanol, water, a mixed solvent of ethanol and water or the like. The mulberry bark extract can also be obtained by a conventional manner using ethanol, water, a mixed solvent of ethanol or water or the like as an extracting solvent.

The amount of these antibacterial plant extracts are not particularly limited insofar as it does not lower the desired effect of the present invention. For example, the antibacterial plant extract are added in an amount of preferably about 0.001–5% by weight, more preferably about 0.01–0.5% by weight, on a dry weight basis as the extract, based on the total amount of the composition.

The composition of the present invention may suitably contain, in addition to the above-mentioned ingredients, pH adjusting agents, organic acids, sugar alcohols, sweeteners, flavoring agents, vitamins, vitamins relating to bone metaboolism, antioxidants, excipients, solubilizing agents, binding agents, lubricants, suspending agents, wetting agents, coating materials, taste improving agent, smell improving agent, coloring agents, preservatives and the like. In addition to these additives, the composition may suitably contain other additives, foodstuffs and the like which are usually used for pharmaceutical compositions, oral compositions or food preparations. Examples of these materials include the following:

Examples of the pH adjusting agents include lactic acid, pantothenic acid, phosphate, malic acid, citric acid and the like.

The vitamins may be any vitamin other than that for use in the present invention, i.e., vitamin C and its salts, vitamin E, vitamin A and beta-carotene. For example, vitamin D group, vitamin K group, vitamin P and the like may be added to the composition of the invention.

Examples of the excipients include sucrose, lactose, starch, glucose, crystalline cellulose, mannitol, sorbitol, xylitol, erythritol, palatinit, palatinose, maltitol, trehalose, lactitol, reduced starch sugar, reduced iso maltooligosaccharide, coupling sugar, gum base, cetyl methyl cellulose, light anhydrous silicic acid, magnesium aluminate, metasilicic acid calcium aluminate, sodium hydrogencarbonate, calcium phosphate and the like.

Examples of the solubilizing agents include alcohols, esters, polyethylene glycol derivatives, sorbitan fatty acid esters, sulfated fatty alcohols and the like.

Examples of the binding agents include cellulose derivatives, carrageenan, sodium alginate, sodium polyacrylate, polylactic acid, polyglycolic acid, xanthan gum, gum arabic, gelatin and the like.

Examples of the lubricants include magnesium stearate, talc, hardened oils and the like.

Examples of the suspending agents or wetting agents include coconut oil, olive oil, sesame oil, peanut oil, parsley oil, parsley seed oil, calcium lactate, safflower oil, soybean phospholipid, glycerin, sorbitol, propylene glycol, ethylene glycol and the like.

Examples of the coating materials include cellulose acetate phthalate and like carbohydrate derivatives; copolymers of acrylic acid (e.g., methyl acrylate), copolymers of methacrylic acid (e.g., methyl methacrylate) and the like.

The composition of the invention may further contain, as a taste improving agent or an smell improving agent, saccharin sodium, acesulfam K, sucralose, aspartame, stevia extract, granulated sugar, powder sugar, starch syrup, common salt, orange oil, water-soluble glycyrrhiza extract, menthol, eucalyptus oil and the like. These additives are sometimes contained in the composition as sweeteners, flavoring agents, colorants or preservatives.

Other ingredients which can be added to the composition of the present invention include lysine, magnesium salts, soybean isoflavones, glycyrrhizin and the like.

The composition of the present invention may contain the various known ingredients mentioned in the above depending on its form, and may be prepared in various forms or formulations as food compositions, oral compositions and pharmaceutical compositions.

The food composition may be prepared, for instance, in the forms of troches, tablets, capsules, granules, powdered juice, chewing gums, candies, gummy candies and the like.

In the present invention, by "capsule" is meant a composition consisting of a capsule film prepared by adding a plasticizer such as glycerin, sorbitol and the like to a base material such as gelatin, and a liquid or gelatinous content enclosed in the capsule film. The capsule film may be constituted of a soft inner capsule film containing gelatin and the like as a base material, and a hard outer capsule film containing saccharide and the like as a base material. In the present invention, especially preferable is a grain capsule which comprises the liquid content and the capsule film comprising the inner capsule film and outer capsule film as described in the above.

The forms of the food composition of the present invention may be any form which at least allows a person to swallow down the above-mentioned active ingredients, that is, the extract containing the natural polyphenol and the vitamins for use in the present invention. The gum base of the chewing gum and the like need not be swallowable.

Further, the food composition of the invention may be prepared as a beverage by dissolving the ingredients or enclosing the ingredients in gel-like beads and suspending the beads.

The form of the oral composition is not limited insofar as it can be applied to the oral cavity. Examples of the oral composition include dentifrices, mouthwashes, troches, oral pastes, gels and the like. Examples of the formulation of the pharmaceutical composition include tablets, pills, powders, liquids, suspensions, emulsions, granules, capsules and the like.

The composition of the invention can be prepared by mixing the extract containing the natural polyphenol and the vitamins for use in the present invention or by mixing with other ingredients together or separately. The composition can be mixed by a conventional manner depending on its form or formulation.

The amount of the food composition of the invention to be taken is not limited and can be appropriately determined depending on the form of the food, the age, body weight, sex and health status of a person and the like. Generally, it is desirable that the composition is taken in an amount of about 0.00001–1 g (by dry weight) as the total amount of an extract containing the natural polyphenol which is the active ingredient and the vitamins for use in the present invention, per day per 1 kg of body weight of a person.

The dose of the pharmaceutical composition of the invention is not limited and can be suitably determined depending on the form of the composition, the age, body weight, sex and degree of the disease of a person and the like. It is desirable that a daily dose is about 0.00001–1 g per 1 kg of body weight, as the total weight of the extract (dry weight) containing the natural polyphenol which is the active ingredient and the vitamins for use in the present invention.

The method for administering the pharmaceutical composition is not limited and can be methods suitable for the formulations and the like. In cases of the above-mentioned tablets, pills, powders, liquids, suspensions, emulsions, granules and capsules, for example, the pharmaceutical composition is administered orally.

The composition of the invention prepared by the aforementioned methods is used in combination with at least one member selected from the group consisting of vitamin C (and its salts), vitamin E, vitamin A and beta-carotene and the polyphenol extract of natural origin, whereby the MMPs inhibitory effects of the composition are increased and high preventive effects on periodontosis can be imparted to the composition. In addition, the composition of the present invention uses the polyphenol extract of natural origin which has few side effects when taken. Thus, the composition of the present invention has greater safety and can be taken for a longer period than synthetic MMPs inhibitors.

The composition of the invention has the inhibiting action on the production of MMPs by periodontium cells and the inhibiting action on the proliferation prevention of periodontium cells. These actions of the composition are more effective when receiving the stimulation by nicotine than without the stimulation by nicotine. Therefore, smokers and passive smokers can take or use the composition of the invention more effectively for preventing or treating periodontosis.

As mentioned in the above, the composition of the invention having excellent preventive and therapeutic effects on periodontosis is highly safe and can be used for a long period as a composition for preventing or treating periodontosis.

Furthermore, the composition of the invention, when used as a food composition, is expected to exert preventive or therapeutic effects on periodontosis. Thus, the composition can be taken as functional foods such as health foods, foods for specified health use and the like.

The composition of the invention, when used as an oral composition, is expected to exert excellent preventive or therapeutic effects on periodontosis, and thus can also be used as a quasi-drug (iyaku-bugaihin).

Moreover, it is also expected that taking or using the food composition or the oral composition of the invention during the treatment of periodontosis improves the therapeutic effect.

The food composition or oral composition of the invention, which can be used for preventing or treating periodontosis, is preferably used particularly as a food composition for preventing periodontosis or an oral composition for preventing periodontosis, wherein the composition containing (A) at least one member selected from the extracts containing the natural polyphenol and (B) at least one member selected from the group consisting of vitamin C and its salts, vitamin E, vitamin A and beta-carotene.

As aforementioned, the composition which comprises the extract containing the natural polyphenol and one or more kinds of vitamin C (and its salts), vitamin E, vitamin A and beta-carotene has a strengthened inhibitory effect on MMPs. The composition also has greater safety and can be used for a long period because it uses the polyphenol extract of natural origin which has few side effects by taking than the synthetic MMPs inhibitors. For this reason, the composition can be used as an MMPs inhibitor. Therefore, the composition, which comprises at least one extract containing the natural polyphenol and at least one member selected from the group consisting of vitamin C and its salts, vitamin E, vitamin A and beta-carotene (the vitamins for use in the present invention), can also be used as an MMPs inhibitor.

In the MMPs inhibitor, the following condition may be the same as those for the above-mentioned food composition, oral composition or pharmaceutical composition of the invention: the kinds and amounts of the extract containing the natural polyphenol and vitamins such as vitamin C; the kinds and amounts of the antibacterial plant extract and other ingredients; the form and formulation of the MMPs inhibitor; and the preparation method, the intake amount or dose, administration method of the MMPs inhibitor.

The MMPs inhibitor is useful as a food composition, an oral composition or a pharmaceutical composition.

Moreover, the natural polyphenol which is present in the extract containing the natural polyphenol added to the MMPs inhibitor are preferably those having inhibitory activities on the MMPs derived from cells such as periosteum and articular cartilage tissue in chronic rheumatism and osteoarthritis; cornea tissue; periodontium; carcinoma tissue and the like, particularly on the MMPs derived from periodontium cells. Hence, the MMPs inhibitor is expected to demonstrate remarkably high inhibitory activities on the MMPs derived from these cells.

The composition of the invention has excellent preventive or therapeutic actions on periodontosis. In addition, the composition of the invention uses the extract containing the natural polyphenol having fewer side effects when taken than synthetic MMPs inhibitors. Therefore, the composition of the invention is highly safe, usable for a long period of time and effective as a food composition, an oral composition or a pharmaceutical composition for preventing or treating periodontosis.

Furthermore, the composition of the invention can be more effectively used by smokers and passive smokers to prevent or treat periodontosis.

BEST MODE FOR CARRYING OUT THE INVENTION

The present invention is described more specifically with Examples and Comparative Examples below. The present invention is not limited to these Test Examples and Examples.

TEST EXAMPLE 1

The inhibitory effects of the extracts containing the natural polyphenols described below in "1. Material" on MMP (collagenase, gelatinase) derived from organism associated with the destruction of periodontium were examined.

1: Material 1-1: Tested Extract

Grape seed extract (trade name: Gravinol; manufactured by KIKKOMAN CORPORATION)

Tea extract (trade name: Sunphenon; manufactured by TAIYO KAGAKU CO., LTD.)

Blueberry extract (manufactured by Indina Corporation)

Silymarin extract (manufactured by Indina Corporation)

1-2: Positive control

Tetracycline 1-3: Collagenase

As collagenase were used two kinds of collagenase mentioned in the following.

The collagenase derived from human gingiva fibroblasts (hereinafter abbreviated as "HGF cell") for use in this test was prepared in the following manner: human procollagenase which was produced in Dulbecco modification MEM culture medium of non-blood serum using the HGF cells was refined using CM Sepharose™ (manufactured by Pharmacia Company) and zinc chelating Sepharose™ (manufactured by Pharmacia Company). The resulting substance was dissolved in a buffer solution and then was activated. The activation was carried out by incubating using aminophenyl acetic acid mercury (manufactured by Sigma Co.) as an activator at 37° C. for 4 hours.

Further, the collagenase derived from human gingival epithelium cell (hereinafter abbreviated as "HGK cell") for use in this test was prepared in the following manner: Human procollagenase was produced in the culture medium for epithelium of non-blood serum using the HGK cells. The produced human procollagenase was refined using CM Sepharose™ (manufactured by Pharmacia Company) and zinc chelating Sepharose™ (manufactured by Pharmacia Company). The refined human procollagenase was dissolved in a buffer solution, which was then activated in the foregoing manner.

1-4: Gelatinase

As the gelatinase were used those derived from the HGF cells and HGK cells.

The gelatinases derived from HGF cells and HFK cells which were used in this test were prepared in the following manner: Human progelatinase was produced using the HGF cells in Dulbecco modification MEM culture medium of the non-blood serum. Meanwhile, human progelatinase was produced using the HGK cells in the culture medium for the epithelium. These human progelatinases were separately refined using gelatin Sepharose 4B™ (manufactured by Pharmacia Company). The refined human progelatinase were activated in the same manner as the collagenase.

2: Test Method 2-1: Measurement of Inhibitory Effect on Collagenase

The measurement of the inhibitory effects on collagenase of the extract containing the natural polyphenol of the above 1-1 was conducted by determining the collagenase activity of the extract. The measurement of the collagenase activity was carried out by the method of Nagai et al. (refer to Japanese Journal of Inflammation, Vol.4, page 123, 1984) in which type I collagen (manufactured by Yagai Co.) labeled by fluorescein isothiocyanate is matrix. Specifically, 40 $\mu$l of activated human collagenase (2U/ml), 50 $\mu$g of the matrix and a test substance which was dissolved in 40 $\mu$l of an assay buffer were mixed. The mixture was allowed to react at 37° C for 4 hours. The collagenase activity of the control (free of the test substance) was regarded as 100%. Based on the reduction rate of the collagenase activity when the test substances were added, $IC_{50}$ value, which indicates the amount necessary for inhibiting 50% of collagenase activity, was determined. Furthermore, the positive control, tetracycline, whose inhibitory effect on the collagenase activity was reported, was compared with the tested natural extract.

2-2: Measurement of Inhibitory Effect on Gelatinase

The inhibitory effect of the extract containing the natural polyphenol on the gelatinase of the above 1-1 was measured using type IV collagen (manufactured by Yagai Co.) labeled by the fluorescein isothiocyanate as a matrix. The measurement method was the same as the above method for measuring the inhibitory activity on the collagenase (2-1). However, the reaction temperature was set at 42° C. The measurement was also carried out on tetracycline by the same method.

The measurement results of the enzyme inhibitory activities on the collagenase and gelatinase derived from the HGK cells and the collagenase and gelatinase derived from the HGF cells are shown in Table 1.

TABLE 1

| | | 50% inhibiting concentration ($\mu$g/ml) | | | | |
| | | Collagenase | | Gelatinase | | Inhibitory |
| | Test substance | HGF | HGK | HGF | HGK | effect |
|---|---|---|---|---|---|---|
| Extract containing the natural polyphenol for use in the invention | Grape seed extract | 1.2 | 2.3 | 1.0 | 1.9 | +++ |
| | Tea extract | 5.4 | 6.6 | 7.8 | 8.1 | ++ |
| | Blueberry extract | 9.4 | 11.2 | 6.5 | 7.3 | ++ |
| | Silymarin extract | 76.0 | 82.4 | 55.0 | 62.4 | + |
| Comparative compound | Tetracycline | 2.5 | 3.2 | 8.7 | 9.2 | +++ |

HGF: Human gingiva fibroblast  
HGK: Human gingival epithelium  
+++: Very effective  
++: Effective  
+: Slightly effective  
−: Not effective The MMP inhibitory effects were found in the extracts containing the natural polyphenol for use in the present invention, i.e., the grape seed extract tea extract, blueberry extract and silymarin extract. In particular, the MMP inhibitory activity of the grape seed extract was found to be equal to or greater than that of tetracycline which is known as a collagenase inhibitor.

In Test Examples 2–4 below, Examples 1–4 were prepared by adding vitamin C or vitamin E respectively to the grape seed extract, tea extract, blueberry extract and silymarin extract.

In addition, Comparative Example 1 and Comparative Example 2 were prepared by using only vitamin C or vitamin E. Comparative Example 3 and Comparative Example 4 were prepared by combining the grape seed extract or tea extract with coenzyme Q10.

TEST EXAMPLE 2

The inhibitory effects on the collagenase production by human gingiva fibroblasts and human gingival epithelium cells were examined.

1: Material

The same materials as in Test Example 1 were used with the exception of using vitamin C and vitamin E, as tested vitamins, and using coenzyme Q10 in Comparative Examples 3 and 4.

The amount of the used grape seed extract, tea extract, blueberry extract and silymarin extract was 100 $\mu$g/ml, respectively. The amount of vitamin C or vitamin E used in Comparative Examples 1 and 2 was 50 $\mu$g/ml, respectively.

2: The Measurement of Inhibitory Effect on Collagenase Production by Cells

The HGF cells and HGK cells were inoculated into separate 96-well plates for tissue culture in an amount of 10,000 cells/well, and were incubated at 37° C. for 1 day. Then, the incubated HGF cells were diluted in a Dulbecco modification MEM culture medium (DMEM) containing the test substance and 1% fetal bovine serum, while the incubated HGK cells were diluted in a culture medium for epithelium containing the test substance and 1% fetal bovine serum. These cells were incubated on the resulting culture media for 2 days. Thereafter, the media were replaced by DMEM media containing only 1% fetal bovine serum or media for. epithelium containing no blood serum, both media not containing the test substance. The culture media were incubated for 2 days. The amounts of the collagenase which were liberated in these culture media were measured by the method of Nagai et al. described at 2-1 of Test Example 1. Further, the relative proportion of the collagenase activities when the respective test substances were added were obtained, the collagenase activity of the culture medium supernatant of the control (free of the test substance) being 100%. Table 2 shows the measurement results of the inhibitory activities on the MMP production by the HGF cells and HGK cells.

TABLE 2

| | | Test substance | | Inhibitory rate (%) on collagenase production (increase rate of inhibition when used in combination) | |
|---|---|---|---|---|---|
| | | Sample | Additive (50 μg/ml) | HGF | HGK |
| Ex. | 1 | Grape seed extract | None | 30 | 36 |
| | | | Vitamin C | 62 (32) | 58 (22) |
| | | | Vitamin E | 48 (18) | 52 (16) |
| | 2 | Tea extract | None | 25 | 28 |
| | | | Vitamin C | 44 (19) | 39 (11) |
| | | | Vitamin E | 47 (22) | 49 (21) |
| | 3 | Blueberry extract | None | 21 | 18 |
| | | | Vitamin C | 41 (20) | 36 (18) |
| | | | Vitamin E | 32 (11) | 25 (7) |
| | 4 | Silymarin extract | None | 14 | 11 |
| | | | Vitamin C | 32 (18) | 35 (24) |
| | | | Vitamin E | 21 (7) | 24 (13) |
| Comp. Ex. | 1 | Vitamin C | None | — | — |
| | 2 | Vitamin E | None | — | — |
| | 3 | Grape seed extract | Coenzyme Q10 | 32 (2) | 39 (3) |
| | 4 | Tea extract | Coenzyme Q10 | 28 (3) | 29 (1) |

In the above Table, HGF represents human gingiva fibroblasts, and HGK represents human gingiva epithelium.

Increase rate of inhibition rate when used in combination (%) is the difference between the inhibitory rate when the extract containing the natural polyphenol and other ingredients were used in combination and the inhibitory rate when the extract containing the natural polyphenol was used singly. In Examples, the inhibitory rate when the extract containing the natural polyphenol was used singly is also indicated {corresponding to (Additives: None)}.

In Tables, by "-" in Comparative Example 1 and Comparative Example 2 is meant that "no inhibitory effect was found".

It was confirmed that the combined use of the extract containing the natural polyphenol and vitamin C or vitamin E effectively improved the inhibitory activity on the MMP produced by the cells.

The combination of grape seed extracts and coenzyme Q10 is conventionally known. However, as shown in Comparative Example 3, this combination can improve the inhibitory rate only by a few percent. On the contrary, as shown in Example 1, the combined use of the grape seed extract and vitamin C or vitamin E in the present invention can improve the inhibitory rate by a few ten %, indicating the remarkable effect of the combination of the invention. In addition, as well as by the above comined use of the grape seed extract and vitamin C or vitamin E, the similar improving effect on the increasing rate was demonstrated by the combined use of the tea extract and vitamin C or vitamin E compared to the combined use of coenzyme Q10 and tea extract (refer to Example 2 and Comparative Example 4).

TEST EXAMPLE 3

As mentioned in the above, it is reported that nicotine which is the main stimulant in cigarette smoke causes the adverse effect such as the inhibition of periodontium proliferation, increase in collagenase production and the like, which is confirmed by in vitro tests. Then, the examination was conducted on the production inhibitory effect by the combined use of the extract containing the natural polyphenol and vitamin C or vitamin E on the collagenase production by human gingiva fibroblasts and human gingival epithelium cells which was increased by the stimulation of nicotine.

1: Material

As materials, vitamin C or vitamin E was used as tested vitamin. Other materials were the same as those used in Test Example 1.

2: The Measurement of Inhibitory Effect on Collagenase Production by Cells Stimulated by Nicotine Measurements were carried out by the method described in Test Example 2. However, to the culture medium was added 0.05% nicotine, together with the test substance and 1% fetal bovine serum. The collagenase activity of the culture medium supernatant of the control (the culture medium containing only nicotine) was regarded as 100%, and the relative proportion of the collagenase activity when the test substances were added was determined. The results are shown in Table 3.

TABLE 3

| | | Test substance | | Inhibitory rate (%) on collagenase production (increase rate of inhibition when used in combination) | |
|---|---|---|---|---|---|
| | | Sample | Additive (50 μg/ml) | HGF | HGK |
| Ex. | 1 | Grape seed extract | None | 15 | 21 |
| | | | Vitamin C | 55 (40) | 48 (27) |
| | | | Vitamin E | 42 (27) | 32 (11) |
| | 2 | Tea extract | None | 11 | 13 |
| | | | Vitamin C | 48 (37) | 39 (26) |
| | | | Vitamin E | 45 (34) | 43 (30) |
| | 3 | Blueberry extract | None | 8 | 12 |
| | | | Vitamin C | 37 (29) | 41 (29) |
| | | | Vitamin E | 41 (33) | 40 (28) |
| | 4 | Silymarin extract | None | 5 | 7 |
| | | | Vitamin C | 37 (32) | 35 (28) |
| | | | Vitamin E | 35 (30) | 32 (25) |
| Comp. Ex. | 1 | Vitamin C | None | — | — |
| | 2 | Vitamin E | None | — | — |

In the above Table, HGF represents human gingiva fibroblasts, and the HGK represents human gingival epithelium cells.
Increase rate of inhibition when used in combination (%) is the difference between the inhibitory rate when the extract containing the natural polyphenol and other ingredients were used in combination and the inhibitory rate when the extract containing the natural polyphenol was used singly. In Examples, the inhibitory rate when the extract containing the natural polyphenol was used singly is also indicated {corresponding to (Additives: None) }.
In the above Table, by "—" in Comparative Example 1 and Comparative Example 2 is meant that "no inhibitory effect was found".

It was confirmed that the addition of the nicotine increases the collagenase production by the tested cells (increase rate:380% of the medium with no nicotine added), but the combined use of the extract containing the natural polyphenol and vitamin C or vitamin E shows an excellent inhibitory activity on the collagenase production increased by the stimulation of nicotine.

Moreover, it was confirmed that the inhibitory activity on the collagenase production by the cells stimulated by nicotine was further increased by the combined use, compared to the results of Test Example 2 (Table 2) to which nicotine was not added.

TEST EXAMPLE 4

Furthermore, examinations were conducted on the effect of the combined use of the natural extracts described in the above Test Example 1 and vitamin C or the like concerning the cell proliferation activity suppressed by the stimulation of nicotine.

1: Material

As materials, vitamin C or vitamin E was used as tested vitamin. Other materials were the same as in Test Example 1.

2: Measurement of the Effect of Nicotine Stimulation on Cell Proliferation

HGF cells and HGK cells were inoculated into separate 96-well plates for tissue culture in an amount of 5,000 cells/well. These HGF cells and HGK cells were incubated at 37° C. for 1 day. Then, the incubated HGF cells were diluted in a Dulbecco modification MEM culture medium containing the test substance, 0.05% nicotine and 1% fetal bovine serum, while the incubated HGK cells were diluted in a culture medium for epithelium containing the test substance, 0.05% nicotine and 1% fetal bovine serum. The cells were incubated on the media for 5 days, and the cell proliferation activities of the cells were observed. Meanwhile, as a control was used the culture medium to which only nicotine was added. After the test substances were cultivated for 5 days, the cells were fixed in a 10% formalin solution and staining in crystal violet. The absorbance of the resulting cells at 590 nm was determined to calculate the population of the cells. The relative proportion of the test substances when the value of the control (culture medium to which only nicotine was added) was 100% was obtained. The measurement results of the effects on the cell proliferation activities of the HGF cells and HGK cells stimulated by nicotine are shown in Table 4.

TABLE 4

| | Test substance | | Proliferation rate of nicotine-stimulated cells (%) (increase rate of proliferation rate when used in combination) | |
|---|---|---|---|---|
| | Sample | Additive (50 μg/ml) | HGF | HGK |
| Control | Culture medium containing only nicotine | None | 100 | 100 |
| Ex. 1 | Grape seed extract | None | 125 | 131 |
| | | Vitamin C | 165 (40) | 149 (18) |
| | | Vitamin E | 159 (34) | 152 (21) |
| 2 | Tea extract | None | 115 | 124 |
| | | Vitamin C | 131 (16) | 147 (23) |
| | | Vitamin E | 142 (27) | 157 (33) |
| 3 | Blueberry extract | None | 109 | 113 |
| | | Vitamin C | 124 (15) | 131 (18) |
| | | Vitamin E | 135 (26) | 146 (33) |
| 4 | Silymarin extract | None | 113 | 109 |
| | | Vitamin C | 146 (33) | 133 (24) |
| | | Vitamin E | 122 (9) | 125 (16) |
| Comp. Ex. 1 | Vitamin C | None | — | — |
| Comp. Ex. 2 | Vitamin E | None | — | — |

In the above Table, HGF represents human gingiva fibroblast, and HGK represents human gingival epithelium cell.
Increase rate of inhibition when used in combination (%) is the difference between the proliferation rate when the extract containing the natural polyphenol and other ingredients were used in combination and the proliferation rate when the extract containing the natural polyphenol was used singly. In Examples, the reproductive rate when the extract containing the natural polyphenol was used singly is also indicated {corresponding to (Additives: None)}.
In the above Table, by "—" in Comparative Example 1 and Comparative Example 2 is meant that "no difference from the control was observed".

It was confirmed that the addition of the nicotine to the culture medium decreases the cell proliferation (52% reduction of the medium with no nicotine added), but the combined use of the extract containing the natural polyphenol and vitamin C or vitamin E increases the inhibitory activity on the cell proliferation inhibition stimulated by nicotine.

Formulation examples of the composition of the invention are described below. These compositions are prepared by a conventional manner unless otherwise stated.

FORMULATION EXAMPLE 1

Chewing Gum

A chewing gum was prepared using grape seed extract, vitamin E, tea extract and oil-soluble glycyrrhiza extract according to the following formula:

| | |
|---|---|
| Calcium carbonate | 5.00 |
| Grape seed extract | 2.00 |
| Vitamin E | 0.01 |
| Tea extract | 1.00 |
| Oil-soluble glycyrrhiza extract | 0.05 |
| Gum base | 27.00 |
| Erythritol | 10.00 |
| Xylitol | 38.00 |
| Maltitol | 12.00 |
| Flavor | q.s. |
| Total | 100.00 part by weight |

FORMULATION EXAMPLE 2

Grain Capsule

A capsule content liquid (60 parts by weight) was enclosed in an inner capsule film (40 parts by weight)

consisting of gelatin and sorbitol. The inner capsule was further provided with a sugar coating thereon with an outer capsule film (110 parts by weight) comprising saccharide, giving a grain capsule.

| Capsule content liquid | |
|---|---|
| Vitamin C | 7.2 |
| Vitamin E | 2.4 |
| Grape seed extract | 12.0 |
| Tea extract | 12.0 |
| Glycerin ester of fatty acid | 1.0 |
| Safflower oil | q.s. |
| Total | 60 parts by weight |
| Inner capsule film | |
| Gelatin | 36.0 |
| Sorbitol | q.s. |
| Total | 40.0 part by weight |
| Outer capsule film | |
| Oil-soluble glycyrrhiza extract | 0.3 |
| Egg shell calcium | 1.0 |
| Aspartame | 0.1 |
| Gum arabic | 0.6 |
| Gelatin | 0.2 |
| Flavor | 0.4 |
| Carnauba wax | 0.1 |
| Shellac | 0.3 |
| Palatinit | q.s. |
| Total | 110.0 part by weight |

FORMULATION EXAMPLE 3

Tablet

A tablet was prepared using vitamin C, vitamin E, grape seed extract, tea extract and oil-soluble glycyrrhiza extract according to the following formula:

| | |
|---|---|
| Vitamin C | 9.0 |
| Powdered vitamin E | 1.0 |
| (containing 20% of d-α-tocopherol) | |
| Grape seed extract | 12.0 |
| Tea extract | 12.0 |
| Oil-soluble glycyrrhiza extract | 1.0 |
| Polydextrose | 7.0 |
| Sugar ester | 2.0 |
| Flavor | 1.0 |
| Xylitol | 15.0 |
| Palatinose | 40.0 |
| Total | 100.0 parts by weight |

FORMULATION EXAMPLE 4

Sugar-coated Tablet

A oral refreshing agent was prepared using a tablet portion (200 parts by weight) containing vitamin C, vitamin E, vitamin A, grape seed extract and tea extract; and a sugar coating portion (130 parts by weight) containing oil-soluble glycyrrhiza extract by coating the tablet portion with the sugar coating portion.

| Tablet portion | |
|---|---|
| Vitamin C | 5.00 |
| Vitamin E | 1.50 |
| Vitamin A | 0.50 |
| Grape seed extract | 8.50 |
| Tea extract | 8.50 |
| Sugar ester | 1.00 |
| Guar gum | 0.20 |
| Aspartame | 0.01 |
| Flavor | 1.00 |
| Palatinose | q.s. |
| Total | 100.00 part by weight |
| Sugar coating portion | |
| Oil-soluble glycyrrhiza extract | 0.12 |
| Tricalcium phosphate | 1.00 |
| Aspartame | 0.01 |
| Gum arabic | 0.50 |
| Flavor | 0.40 |
| Carnauba wax | 0.10 |
| Shellac | 0.20 |
| Maltitol | q.s. |
| Total | 100.00 parts by weight |

FORMULATION EXAMPLE 5

Candy

A candy containing grape seed extract, tea extract, vitamin C and mulberry bark extract was prepared according to the following formula:

| | |
|---|---|
| Grape seed extract | 1.0 |
| Tea extract | 1.0 |
| Vitamin C | 5.0 |
| Mulberry bark extract | 0.1 |
| Xylitol | 8.0 |
| Maltitol | 10.0 |
| Aspartame | 0.1 |
| Flavor | 0.2 |
| Palatinit | q.s. |
| Total | 100.00 parts by weight |

FORMULATION EXAMPLE 6

Bead-in Drink

First, a gel in which the ingredients listed below are uniformly dissolved was added dropwise to a 5% calcium lactate solution, giving ball-shaped vitamin beads.

| Vitamin beads formulation | |
|---|---|
| Vitamin E | 0.10 |
| (containing 67% of d-α-tocopherol) | |
| Oil-soluble glycyrrhiza extract | 0.02 |
| Erythritol | 15.00 |
| Stevia | 0.05 |
| Sodium alginate | 1.00 |
| Pigment | 0.05 |
| Deionized water | q.s. |
| Total | 100.00 parts by weight |

Then, the above vitamin beads were added to the drink prepared according to the following formula.

| | |
|---|---|
| Grape seed extract | 0.05 |
| Vitamin C | 1 |
| 1% Gellan gum | 10 |
| Erythritol | 15 |
| Stevia | 0.1 |
| Flavor | 0.2 |
| Vitamin beads | 7 |
| 50% Citric acid solution as much as is needed to adjust pH to | 3.7 |
| Deionized water | q.s. |
| Total | 100.00 parts by weight |

FORMULATION EXAMPLE 7

Tooth Paste

| | |
|---|---|
| Calcium secondary phosphate | 30.00 |
| Glycerin | 10.00 |
| Sorbitol | 20.00 |
| Sodium carboxymethylcellulose | 1.00 |
| Sodium lauryl sulfate | 1.50 |
| Carrageenan | 0.50 |
| Saccharin sodium | 0.10 |
| Flavor | 1.00 |
| Sodium benzoate | 0.30 |
| Grape seed extract | 0.05 |
| Vitamin E | 0.05 |
| Oil-soluble glycyrrhiza extract | 0.05 |
| Water | q.s. |
| Total | 100.00 parts by weight |

FORMULATION EXAMPLE 8

Mouthwash

| | |
|---|---|
| Ethanol | 10.00 |
| Glycerin | 5.00 |
| Citric acid | 0.01 |
| Sodium citrate | 0.10 |
| Polyoxyethylene hydrogenated castor oil | 0.50 |
| Methyl p-hydroxybenzoate | 0.10 |
| Flavor | 0.20 |
| Grape seed extract | 0.05 |
| Vitamin E | 0.05 |
| Vitamin C | 0.01 |
| Water | q.s. |
| Total | 100.00 part by weight |

FORMULATION EXAMPLE 9

Troche

| | |
|---|---|
| Maltitol | 21.00 |
| Gum arabic | 1.50 |
| Sucrose fatty acid ester | 2.50 |
| Powdered flavor | 1.00 |
| Citric acid | 4.00 |
| Grape seed extract | 0.10 |
| Vitamin C | 10.00 |
| Oil-soluble glycyrrhiza extract | 0.05 |
| Xylitol | q.s. |
| Total | 100.00 parts by weight |

FORMULATION EXAMPLE 10

Oral Paste

| | |
|---|---|
| Liquid paraffin | 13 |
| Cetyl alcohol | 10 |
| Glycerin | 25 |
| Sorbitan monopalmitate | 0.6 |
| Polyoxyethylene sorbitan monostearate | 5 |
| Sodium lauryl sulfate | 0.1 |
| Benzethonium chloride | 0.1 |
| Methyl salicylate | 0.1 |
| Saccharin | 0.2 |
| Flavor | 0.25 |
| Grape seed extract | 0.10 |
| Vitamin E | 0.05 |
| Oil-soluble glycyrrhiza extract | 0.05 |
| Water | q.s. |
| Total | 100.00 parts by weight |

FORMULATION EXAMPLE 11

Oral Gel

| | |
|---|---|
| Carboxymethylcellulose | 0.2 |
| Glycerin | 40 |
| Grape seed extract | 1 |
| Vitamin E | 0.05 |
| Water | q.s. |
| Total | 100.00 (% by weight) |

FORMULATION EXAMPLE 12

Grain Capsule

A capsule content liquid (60 parts by weight) was enclosed in an inner capsule film (40 parts by weight) consisting of gelatin and sorbitol. The inner capsule film was provided with a sugar coat thereon using an outer capsule film (110 parts by weight) comprising saccharide, giving a grain capsule.

| | |
|---|---|
| Capsule content liquid | |
| Vitamin C | 25.0 |
| Grape seed extract | 10.0 |
| Tea extract | 10.0 |
| Glycerin ester of fatty acid | 1.0 |
| Safflower oil | q.s. |
| Total | 60 parts by weight |
| Inner capsule film | |
| Gelatin | 36.0 |
| Sorbitol | q.s. |
| Total | 40.0 parts by weight |
| Outer capsule film | |
| Oil-soluble glycyrrhiza extract | 0.3 |
| Egg shell calcium | 1.0 |

-continued

| | |
|---|---|
| Aspartame | 0.1 |
| Gum arabic | 0.6 |
| Gelatin | 0.2 |
| Flavor | 0.4 |
| Carnauba wax | 0.1 |
| Shellac | 0.3 |
| Palatinit | q.s. |
| Total | 110.0 parts by weight |

It is to be understood that the above Examples and Formulation Examples describe only particular embodiments of the present invention, and the present invention are not limited to these Examples and Formulation Examples.

What is claimed is:

1. A method for treating periodontosis by ingesting or administering to a subject in need thereof an effective amount of a composition comprising at least one natural polyphenol-containing extract selected from the group consisting of a grape seed extract) a green tea extract, a blueberry extract and a silymarin extract; and at least one member selected from the group consisting of vitamin C and its salts and vitamin E.

2. The method according to claim 1 which further contains an antibacterial plant extract.

3. The method according to claim 2, wherein the antibacterial plant extract is at least one member selected from the group consisting of an oil-soluble glycyrrhiza extract and a mulberry bark extract.

4. The method according to claim 1 wherein the subject in need thereof is a smoker.

5. A method for treating periodontosis which comprises application to oral cavity of a subject in need thereof an effective amount of at least one natural polyphenol-containing extract selected from the group consisting of a grape seed extract, a green tea extract, a blueberry extract and a silymarin extract; and at least one member selected from the group consisting of vitamin C and its salts and vitamin E.

6. The method according to claim 5 wherein the subject in need thereof is a smoker.

7. The method according to claim 1, wherein said at least one natural polyphenol-containing extract is selected from the group consisting of a grape seed extract, a blueberry extract and a silymarin extract.

8. The method according to claim 7, wherein said natural polyphenol-containing extract is a grape seed extract.

9. The method according to claim 5, wherein said at least one natural polyphenol-containing extract is selected the group consisting of a grape seed extract, a blueberry extract and a silymarin extract.

10. The method according to claim 9, wherein said natural polyphenol-containing extract is a grape seed extract.

11. The method according to claim 5 which further comprises an antibacterial plant extract.

12. The method according to claim 11, wherein the antibacterial plant extract is at least one member selected from the group consisting of an oil-soluble glycyrrhiza extract and a mulberry bark extract.

* * * * *